United States Patent
Zordan

(10) Patent No.: US 9,915,674 B2
(45) Date of Patent: Mar. 13, 2018

(54) METHODS AND APPARATUS FOR MEASURING ASPIRATION PRESSURE

(71) Applicant: Siemens Healthcare Diagnostics Inc., Tarrytown, NY (US)

(72) Inventor: Enrico Zordan, Darien, CT (US)

(73) Assignee: Siemens Healthcare Diagnostics Inc., Tarrytown, NY (US)

( * ) Notice: Subject to any disclaimer, the term of this patent is extended or adjusted under 35 U.S.C. 154(b) by 53 days.

(21) Appl. No.: 15/028,823

(22) PCT Filed: Oct. 15, 2014

(86) PCT No.: PCT/US2014/060740
§ 371 (c)(1),
(2) Date: Apr. 12, 2016

(87) PCT Pub. No.: WO2015/057868
PCT Pub. Date: Apr. 23, 2015

(65) Prior Publication Data
US 2016/0258972 A1    Sep. 8, 2016

Related U.S. Application Data

(60) Provisional application No. 61/891,951, filed on Oct. 17, 2013.

(51) Int. Cl.
*G01N 35/10* (2006.01)
*G01F 13/00* (2006.01)
(Continued)

(52) U.S. Cl.
CPC ............ *G01N 35/1016* (2013.01); *B01L 3/02* (2013.01); *B01L 3/021* (2013.01); *G01L 11/04* (2013.01);
(Continued)

(58) Field of Classification Search
CPC ............... G01N 35/0099; G01N 35/10; G01N 35/1009; G01N 35/1016;
(Continued)

(56) References Cited

U.S. PATENT DOCUMENTS

| | | | |
|---|---|---|---|
| 5,730,938 A * | 3/1998 | Carbonari | G01N 35/10 134/170 |
| 5,916,524 A | 6/1999 | Tisone | |
| 5,965,828 A * | 10/1999 | Merriam | G01F 11/00 137/557 |
| 6,589,791 B1 | 7/2003 | Labudde et al. | |
| 8,061,216 B2 | 11/2011 | Jones | |
| 2004/0048393 A1 | 3/2004 | Colin et al. | |
| 2005/0056713 A1 | 3/2005 | Tisone et al. | |
| 2005/0096627 A1 | 5/2005 | Howard | |
| 2006/0109141 A1* | 5/2006 | Huang | G01V 11/002 340/855.4 |
| 2007/0102445 A1 | 5/2007 | Nay et al. | |
| 2007/0177986 A1 | 8/2007 | Leibfried | |
| 2011/0000276 A1* | 1/2011 | Wassermeier | B01L 3/0275 73/1.74 |

(Continued)

OTHER PUBLICATIONS

PCT International Search Report and Written Opinion dated Jan. 15, 2015 (9 Pages).

(Continued)

*Primary Examiner* — Nguyen Ha

(57) ABSTRACT

An aspiration apparatus adapted to allow aspiration verification of a liquid such as of a biological liquid or reagent liquid, especially at low aspiration volumes (e.g., less than 25 μL). The apparatus includes a pump operable at an operating frequency, the pump optionally including a pumping chamber, a probe having a probe interior, a main supply line containing a backing liquid coupled to and extending from the pump and including the probe interior, a striction coupled to the main supply line, or the pump chamber, if present, and a reservoir fluidly coupled to the striction, wherein the striction is sized to minimize backing liquid flow through the striction at one or more disturbance frequencies above the operating frequency. Systems and methods for carrying out the liquid aspiration are provided, as are other aspects.

20 Claims, 6 Drawing Sheets

(51) Int. Cl.
*G01L 11/04* (2006.01)
*B01L 3/02* (2006.01)
*G01N 35/00* (2006.01)

(52) U.S. Cl.
CPC ..... *G01N 35/0099* (2013.01); *G01N 35/1009* (2013.01); *B01L 3/0217* (2013.01); *B01L 2200/146* (2013.01); *B01L 2300/0627* (2013.01); *B01L 2300/12* (2013.01); *B01L 2300/14* (2013.01); *B01L 2400/0487* (2013.01); *B01L 2400/06* (2013.01); *B01L 2400/086* (2013.01); *G01F 13/00* (2013.01); *G01N 2035/1025* (2013.01); *G01N 2035/1034* (2013.01)

(58) Field of Classification Search
CPC . G01N 2035/1034; G01N 2035/10125; G01N 2035/1025; G01F 13/00; B01L 3/02; B01L 3/021; B01L 3/0217
See application file for complete search history.

(56) References Cited

U.S. PATENT DOCUMENTS

| | | |
|---|---|---|
| 2011/0318242 A1 | 12/2011 | Nay et al. |
| 2012/0017704 A1 | 1/2012 | Kirste et al. |
| 2012/0236063 A1* | 9/2012 | Nakazawa ........... B41J 2/16579 347/19 |
| 2015/0276534 A1* | 10/2015 | Dunfee .............. G01N 35/1016 73/700 |

OTHER PUBLICATIONS

Extended EP Search Report dated Oct. 5, 2016 of corresponding European Application No. 14854723.5, 4 Pages.

* cited by examiner

METHODS AND APPARATUS FOR MEASURING ASPIRATION PRESSURE

RELATED APPLICATION

This application claims priority to U.S. Provisional Application Ser. No. 61/891,951 entitled "METHODS AND APPARATUS FOR MEASURING ASPIRATION PRESSURE" filed on Oct. 17, 2013, the disclosure of which is hereby incorporated by reference in its entirety herein.

FIELD

The present invention relates generally to methods and apparatus for sensing pressure during aspiration of liquids in clinical analyzers.

BACKGROUND

In testing within clinical laboratories to measure various chemical constituents of biological fluids obtained from patients, such as whole blood, blood serum, blood plasma, and the like, fully-automated clinical analyzers may be used to improve testing accuracy and cost per test.

Typically, an automated analyzer includes an automated aspirating and dispensing system 100, such as shown in FIG. 1, which is adapted to aspirate a liquid (e.g., a sample of biological liquid 108S or a reagent liquid 107R) from a container (sample container 108 or reagent container 107) and dispense the liquid into a reaction vessel 113 (e.g., a cuvette). The aspirating and dispensing system 100 typically includes a pipetting operation where probe 104 (otherwise referred to as a "pipette") mounted to a robot, performs aspiration and dispensing functions so as to transfer the liquid to the reaction vessel 113.

During the aspiration operation, the robot may position the probe 104 above the container, and descend the probe 104 into the container until the probe 104 is partially immersed in the liquid. A pump is then activated to draw in (aspirate) a portion of the liquid from the container into the interior of the probe 104. The probe 104 is then ascended (retracted) from the container such that the liquid may be transferred to the reaction vessel for testing. During or after the aspiration, an aspiration pressure signal from a sensor 130 may be analyzed to determine any anomalies, i.e., check for the presence of a clog or the presence of air should there be insufficient liquid remaining to carry out the desired aspiration.

Conventional systems may be able to acceptably perform these checks for anomalies when relatively large liquid volumes are aspirated (e.g., 30 µL or greater). However, if the volume of the aspirated sample is relatively small, noise in the pressure signal may dominate and may be so large that it may obscure the information contained in the pressure signal. Accordingly, when the aspirated liquid volume is relatively small, it may become very difficult to robustly verify proper aspiration. Thus, there is a need for improvements in pressure sensing during aspiration, especially when the aspirated volume of the liquid is relatively small.

SUMMARY

In a first aspect, an aspiration apparatus is provided. The aspiration apparatus includes a pump operable at an operating frequency, the pump optionally including a pumping chamber; a probe having a probe interior, a main supply line containing a backing liquid coupled to and extending from the pump, the main supply line including the probe interior, a striction coupled to the main supply line, or the pump chamber, if present, and a reservoir fluidly coupled to the striction, wherein the striction is sized to minimize flow through the striction at one or more disturbance frequencies above the operating frequency.

In another aspect, an aspiration system is provided. The aspiration system includes a probe having a probe interior adapted to aspirate a biological liquid or reagent liquid; a pump having a pumping chamber operable at an operating frequency, a robot coupled to and adapted to move the probe, a main supply line containing a backing liquid coupled to the pumping chamber, the main supply line including the probe interior, a striction coupled to the pumping chamber or main supply line, and a reservoir fluidly coupled to the striction, wherein the striction is sized to decouple the reservoir and minimize flow of backing liquid at one or more disturbance frequencies above the operating frequency.

According to another aspect, a method of aspirating a biological or reagent liquid is provided. The method includes attempting to aspirate a volume of the biological or reagent liquid into a probe by pumping a backing liquid in a main supply line at an operating frequency, measuring pressure in a reservoir decoupled from the main supply line by a striction and providing a measured pressure signal, and verifying the attempting to aspirate the volume of the biological or reagent liquid.

Still other aspects, features, and advantages of the present invention may be readily apparent from the following detailed description by illustrating a number of exemplary embodiments and implementations, including the best mode contemplated for carrying out the present invention. The present invention may also be capable of other and different embodiments, and its several details may be modified in various respects, all without departing from the scope of the present invention. Accordingly, the drawings and descriptions are to be regarded as illustrative in nature, and not as restrictive. The drawings are not necessarily drawn to scale. The invention is to cover all modifications, equivalents, and alternatives falling within the scope of the invention.

BRIEF DESCRIPTION OF THE DRAWINGS

The invention will be better understood by referring to the detailed description taken in conjunction with the following drawings.

DESCRIPTION

In view of the foregoing difficulties, there is an unmet need to accurately determine aspiration quality (e.g., aspiration completeness or incompleteness) when aspirating a liquid, especially relatively-low liquid volumes (e.g., less than about 25 μL). The apparatus, system, and method described herein have utility for use in clinical analyzers and the like for carrying out analyte measurements, assays, immunoassays, or other tests. In particular, the apparatus has particular utility in any system where liquids are aspirated and/or dispensed at low volumes. In one or more embodiments, the liquid may be a liquid reagent or a biological liquid, for example.

One or more embodiments of the invention provide methods, systems, and apparatus that substantially reduce the signal noise present in a measured pressure signal. Accordingly, this provides improved ability to determine aspiration quality, especially during low-volume aspiration. Thus, using embodiments of the present invention may accurately determine aspiration pressure so that a presence of air (e.g., an air bubble) may be readily determined and discriminated. A presence of a clog, other obstruction, foreign material, or the like in the probe may also be determined. To address this need, embodiments of the present invention provide improved apparatus, systems, and methods to detect aspiration pressure. Although embodiments of the present invention enable low-volume discrimination, they also may be used at higher-volume aspiration, as well. For example, embodiments of the present invention may improve volume aspiration discrimination and confidence even at relatively higher aspiration volumes (e.g., above 30 μL).

Figure 1:
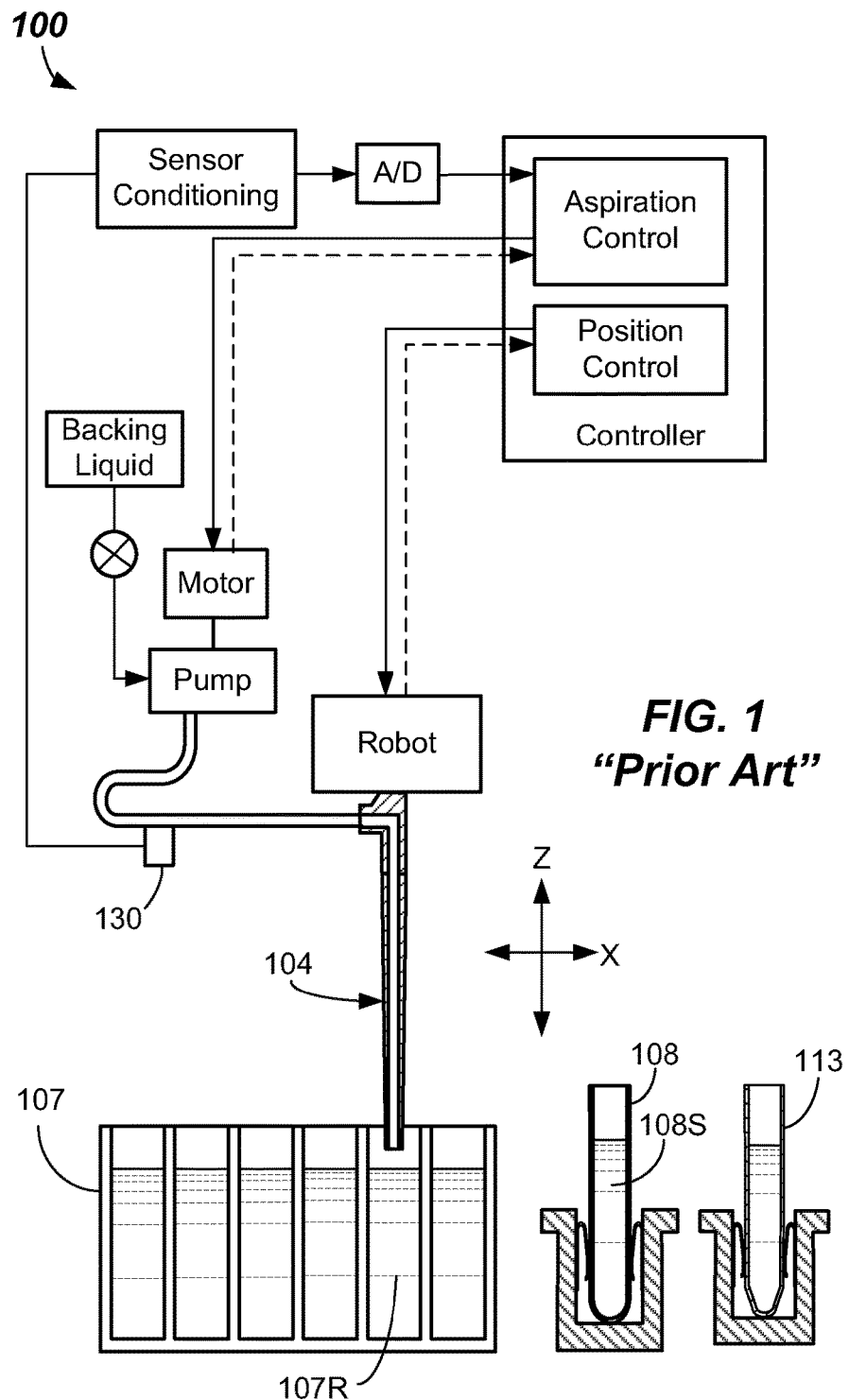
FIG. 1 illustrates a schematic diagram of an aspirating system according to the prior art.

In particular, in prior aspiration apparatus including an aspiration pump, a probe, and tubing (e.g., flexible tubing) coupling the probe to the pump, where a backing liquid for accomplishing the aspiration is water (e.g., purified water), fluid resonances, pump resonances, and other low-frequency resonant noises (collectively, "noise") may dominate the measured pressure signal, when measured conventionally as shown in FIG. 1. Such "noise" may therefore substantially obscure the measured pressure signal with signal noise.

To remove the unwanted signal noise, apparatus, systems, and methods of one or more embodiments of the invention obtain the pressure measurement from a fluid subsystem that is fluidly decoupled the from the main supply line. For example, a reservoir may be fluidly coupled to the main supply line, but decoupled by a striction. Striction may be a small dimension passageway between the main supply line and the reservoir. The striction functions as a fluid filter by fluidly decoupling at least the dominant disturbance of "noise" at undesirable frequencies above the operating frequency from entering the reservoir. A sensor coupled to the reservoir may provide a measured pressure signal. In many cases, the dominant "noise" frequency may be a liquid resonance or other liquid vibration superimposed on the flow within the main supply line.

This fluid decoupling provides additional signal noise reduction that is in addition to conventional sensor conditioning (including anti-aliasing filters and amplifier) that is commonplace for filtering sensor signals in the prior art. Such anti-aliasing filters have a cutoff frequency that is generally far too high to address the low-frequency noise of the type that is present in such liquid aspiration. In particular, the striction is designed to pass frequencies in the range of the operating frequency (e.g., the aspiration frequency), but attenuate and decouple flow of one or more frequencies of noise disturbances, such as above the operating frequency. For example, a dimension (e.g., diameter or length or both) of the striction may be sized that it may have a cutoff frequency that is set at a frequency that is both above the aspiration operational frequency generated by the liquid aspiration event, and is below the frequency or frequencies of the liquid pressure disturbances, or even below a dominant frequency of the disturbance in the main supply line, for example. The dominant frequency may be a liquid resonance or vibration due to pump operational frequencies, motor frequencies, or other system mechanical disturbances.

The apparatus, systems, and methods described herein may be particularly effective for small-volume aspirations of volumes less than about 25 μL, less than about 20 ||L, less than about 15 μL, or even less than about 10 μL. In some embodiments, the apparatus, systems, and methods may be effective to aspirate a biological liquid or reagent liquid and a total aspirated volume of the biological liquid or reagent liquid is between about 1 μL and about 25 μL. In other embodiments, the apparatus, systems and methods may be effective to aspirate a liquid reagent and the total aspirated volume of the liquid reagent is between about 5 μL and about 25 μL. In some embodiments, the pressure measurement is of a backing liquid used as the vehicle for aspirating a biological liquid, the liquid reagent, or other liquid used in a biological testing.

The liquid decoupling (e.g., filtering) may be accomplished by any suitable type of striction. In particular, the striction may be sized in dimension (e.g., diameter and/or length) such that it provides a cutoff frequency that cuts out frequencies that coincide with disturbances from mechanical resonances (e.g., 30 Hz-80 Hz), electrical resonances (e.g., 60 Hz), and dominant frequencies due to liquid resonances (e.g., at about 20 Hz-50 Hz) or other liquid vibrations occurring in the liquid backing that are above the operating frequency. Additionally, the striction is appropriately sized to allow the pressure disturbance frequency generated by an aspiration at the operating frequency to pass through the striction so it may be measured (i.e., the aspiration frequency that is typically less than 10 Hz). "Operating frequency" as used herein is the aspiration frequency, i.e., a frequency of a single aspiration event from beginning to end. One aspiration cycle starts at the beginning of the aspiration stroke of the pump and is completed at an end of the stroke of the pump. Thus, at the beginning there is only backing liquid in the probe and at the end of the cycle, there is an aspirated liquid (e.g., biological liquid or liquid reagent) in the probe. According to embodiments, a full cycle of an aspiration of the liquid (e.g., reagent liquid or biological liquid) may be completed in less than about 300 ms (corresponding to about 3.3 Hz), less than about 200 ms (corresponding to 5.0 Hz), or even less than about 100 ms (corresponding to 10.0 Hz). In some embodiments, the aspiration cycle may be completed in between about 40 ms and about 200 ms (corresponding to between about 25 Hz and about 5 Hz). The operating (aspiration) frequency may be less than about 25 Hz, less than about 10 Hz, less than 5 Hz, less than about 3.3 Hz, or even less than about 1 Hz, for example. The striction may be a relatively small liquid passage.

These and other aspects and features of embodiments of the invention will be described with reference to FIGS. 2-6 herein.

Figure 2:
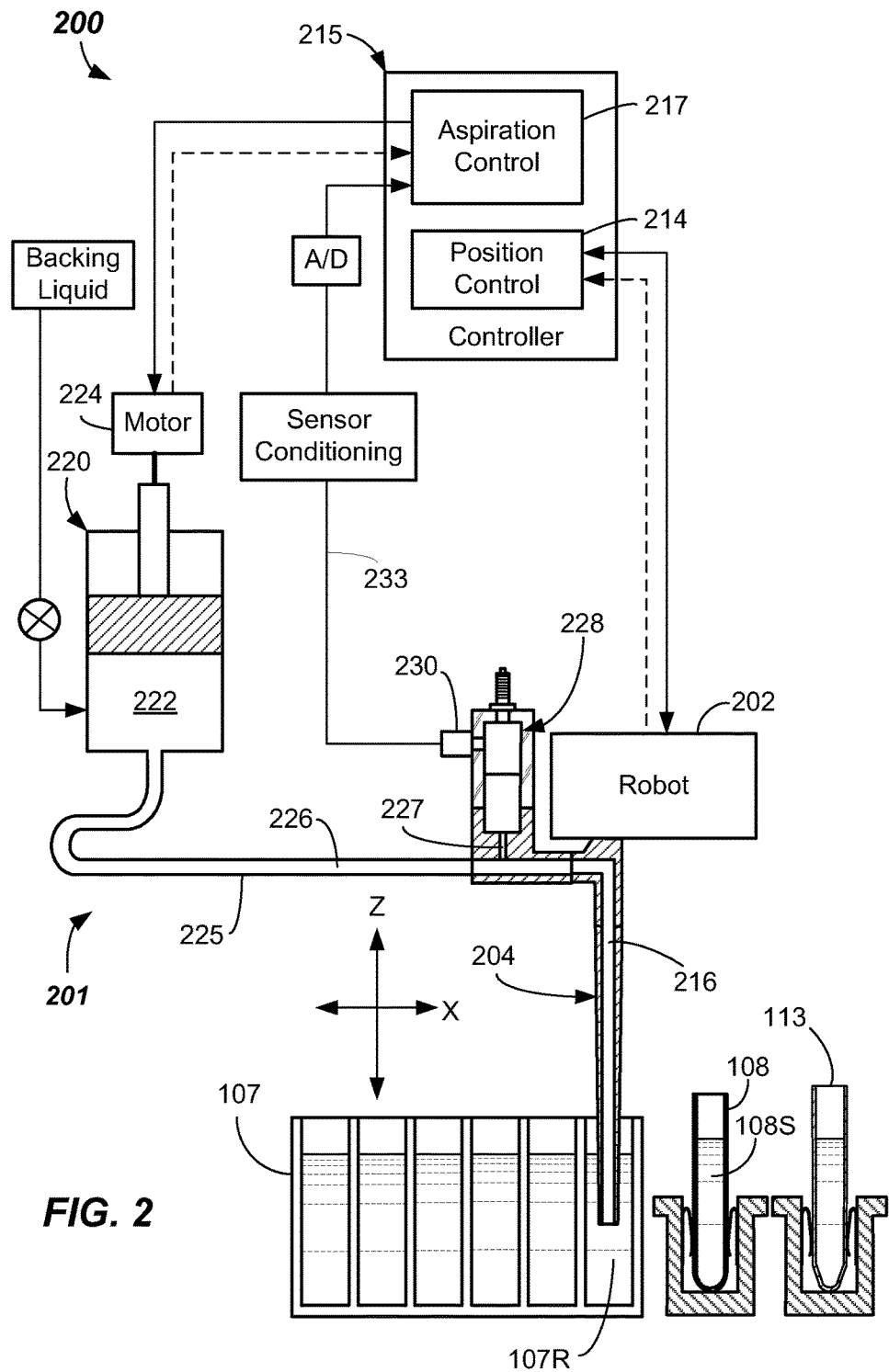
FIG. 2 illustrates a schematic diagram of an aspirating system including an aspirating apparatus according to embodiments.

Referring to FIG. 2, a first embodiment of an aspiration system 200 including an aspiration apparatus 201 is illustrated. The aspiration apparatus 201 may include any suitable robot 202 and a probe 204 adapted to aspirate a liquid. Liquid may also be dispensed by the aspiration apparatus 201. The robot 202 is adapted to carry out motion of the probe 204 in one or more coordinate directions, such as X, Y (into and out of the paper), and/or Z. However, typically, the robot 202 may move the probe 204 in the X and Z directions only.

The robot 202 may include one or more robot components (e.g., robot arm(s), link(s), boom(s), frame (s), or the like) to which the probe 104 may be mounted to accomplish motion thereof. The robot 202 may be operable to descend and ascend the probe 204 into and out of a reagent container 107 containing a volume of a reagent liquid 107R and/or into and out of a sample container 108 containing biological liquid 108S, so that at least some may be aspirated. The biological liquid 108S may be blood, blood serum, plasma, cerebral liquid, spinal liquid, interstitial liquid, urine, or the like. Other liquids may be aspirated. The robot 202 may be suitably actuated under the control of a position control 214 of a controller 215 to impart the desired motions to the probe 204 in one dimension, two dimensions, or three dimensions. Such mechanical systems that are adapted to move the probe 204 may include system and/or component mechanical resonances or vibrations and may impart system noise (e.g., pressure perturbations in the backing liquid) from the operation thereof.

For example, the robot 202 may be operated to move the probe 204 from the reagent container 107 to a reaction vessel 113 (e.g., a cuvette), and/or from the sample container 108 to the reaction vessel 113. The aspirator apparatus 201 may be provided to aspirate the desired liquid (e.g., reagent liquid 107R, biological liquid 108S, or other suitable liquid) into the interior 216 of the probe 204. The aspirated volume may be less than about 25 μL, less than about 20 μL, less than about 15 μL, or even less than about 10 μL in some embodiments. Prior systems were unable to discriminate effectively at such low volumes.

The aspirator apparatus 201 may include a pump 220 that may include a pumping chamber 222. For example, pump 220 may be a piston-type pump that may be driven by a suitable motor 224, such as a stepper motor. Other types of pumps, including non-chambered pumps, may be used. The pump 220 may be adapted to cause a liquid (e.g., a biological liquid 108S, reagent liquid 107R, or the like) to aspirate into the interior 216 of the probe 204. The aspiration takes place at the operating frequency (e.g., at the aspiration rate) as described above via operation of the pump 220, which creates an internal pressure (e.g., suction) to cause flow and aspirate the liquid having a defined frequency (at the aspiration frequency). A range of aspiration rates achievable by the aspiration apparatus 201 are between about 20 microliters per second and about 500 microliters per second, which creates a pressure signal having a relatively short duration, in the range of operating frequencies of a single aspiration described above. The motor 224 of the pump 220 may be a source of system noise causing pressure variations or flow superimposed vibrations in a backing liquid 226 contained within the main supply line 225. Main supply line 225 may include a flexible tube section along most of its length in some embodiments. Flexible tube section may be a section of hollow Teflon tube or other suitably flexible conduit. Main supply line 225 includes the supply line section extending from the pump 220 and also includes the interior 216 of the probe 204.

The pump 220 may be configured to have excellent precision at low volume aspiration and dispensing (e.g., less than 25 μL). In the depicted aspiration apparatus 201, when operated in a low-volume aspiration mode, a total aspirated volume per aspiration cycle may be about 25 μL or less, or even about 20 μL or less, or even about 15 μL or less, or even about 10 μL or less in some embodiments. It should be recognized that the aspiration apparatus 201 is capable of excellent discrimination at higher aspiration volumes, as well (e.g., greater than 30 μL). One aspiration cycle starts at the beginning of the aspiration stroke of the pump 220 and is completed at an end of the stroke of the pump 220. According to embodiments, the aspiration flow rate may be less than about 500 μL/s, even less than about 200 μL/s, even less than about 100 μL/s, or even less than about 60 μL/s in some embodiments.

The pump 220 may be fluidly coupled to the probe 204 by the flexible tube section of the main supply line 225. The flexible tube section and the interior 216 of the probe 104 making up the main supply line 225 may be filled with a backing liquid 226 (e.g., purified water) to provide a suitable liquid backing to generate an appropriate vacuum pressure to allow aspiration of the various liquids (e.g., reagent liquid 107R, biological liquid 108S, and/or the like) into the interior 216 of the probe 204 for transfer to the reaction vessel 113 for suitable testing. The length of the flexible tubing section may be between about 0.5 m and about 1.5 m in some embodiments. Other lengths may be used. The main supply line 225 (including flexible tubing section and interior 216 of the probe 204) and pumping chamber 222 of the pump 220 may be filled with the backing liquid 226.

Aspiration control of the controller 215 may be adapted and operational to control the motor 224 and thus the pump 220 to draw in (e.g., aspirate) a desired amount of the liquid (e.g., reagent liquid 107R or biological liquid 108S) into the interior 216 of the probe 204. Aspiration control of the controller 215 may also control the dispensing operations performed by the aspiration apparatus 201. The aspiration apparatus 201 may include other conventional components, such as one or more valve(s), accumulator(s), distributors, or other hydraulic components (not shown) to effectuate the liquid aspiration. Any suitable apparatus for aspirating the liquid into the probe 204 may be used. For example, aspirating and dispensing systems, which may be used with the present invention, are described in U.S. Pat. Nos. 7,867,769; 7,634,378; 7,477,997; 7,186,378; 7,150,190; and 6,370,942.

Operation of the pump 220 at the operating frequency together with the stiffness of the flexible tubing section and other compliances and components within the aspiration apparatus 201 may cause one or more system liquid resonances, disturbances, or superimposed vibrations within the backing liquid 226. These liquid resonances, disturbances, or superimposed vibrations do not appreciably impact the measured pressure signal in embodiments of the present invention.

Figure 3:
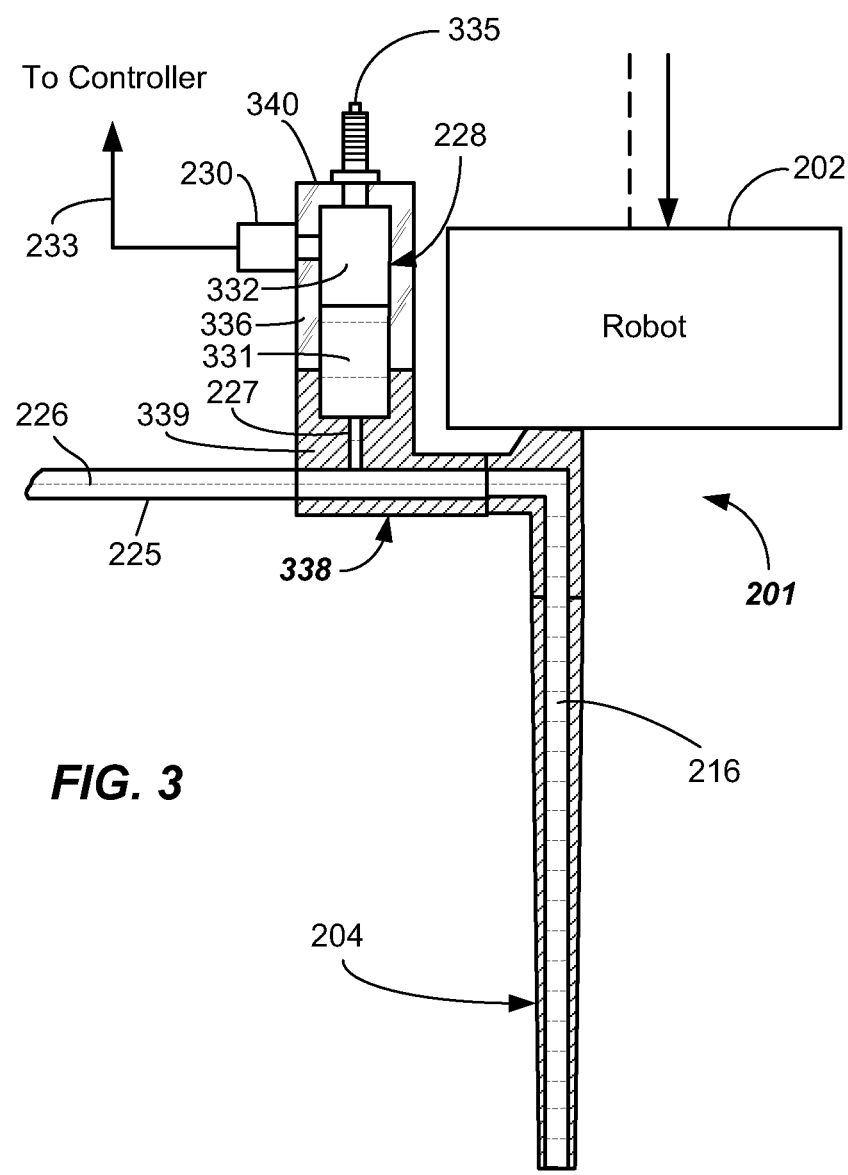
FIG. 3 illustrates a schematic diagram of a manifold of an aspirating apparatus according to embodiments.

In particular, to minimize these impacts, the main supply line 225 containing the backing liquid 226, which is coupled to, and extends from, the pump 220 and pumping chamber 222 (if present in the pump 220), includes a striction 227. The striction 227 is fluidly coupled to the main supply line 225 (which includes the flexible tube section and the interior 216) in the depicted embodiment, and also fluidly connects to a reservoir 228, as shown in FIGS. 2 and 3. Thus, the striction 227 provides a flow passageway connecting between the main supply line 225 and the reservoir 228. The striction 227 is sized to minimize flow of the backing liquid 226 at one or more disturbance frequencies above the operating frequency (e.g., liquid resonances, liquid disturbances, and/or liquid vibrations in the main supply line 225) of the aspirating apparatus 201. For example, the striction 227 may be sized to substantially minimize liquid flow at above about 50 Hz. The diameter and/or length of the striction 227 may be appropriately sized (e.g., initially selected), such as by modeling or experiments. The striction 227 may include larger diameter regions and a smaller diameter region or regions in some embodiments. In some embodiments, the striction 227 may have a striction cross-sectional area (As) that is less than a main supply line cross-sectional area (Am) of the main supply line 225, i.e., As<Am. In one or more embodiments, the striction 227 may include a diameter of between about 1 mm and about 1.5 mm, and a length of between about 2 mm and about 4 mm. Other suitable dimensions may be used.

In the depicted embodiment, a sensor 230 may be coupled to the reservoir 228. The sensor 230 may be any suitable sensor adapted to measure pressure in the reservoir 228 and generate a measured pressure signal in the range of the operating frequency in line 233. As shown in FIG. 3, the reservoir 228 may comprise a liquid-containing portion 331 and a gas-containing portion 332. Liquid-containing portion 331 and gas-containing portion 332 may abut at a liquid-gas interface. Because the pressure is measured by the sensor 230 coupled to the reservoir 228, which is removed and fluidly decoupled from the main supply line 225 by the striction 227, the sensor 230 produces a measured sensor signal in line 233 that is substantially devoid of any disturbances produced by flow in the main supply line 225 that is above the operating frequency (e.g., above 50 Hz). In the depicted embodiment, the reservoir 228 may include a valve 335 adapted to apply gas pressure to the reservoir 228. A bike valve or other gas input valve may be used. In some embodiments, the reservoir 228 may include a wall 336 of a transparent or translucent material. This allows the liquid-gas interface to be viewed, and may allow the liquid-gas interface to be set at a desired height within the reservoir 228 through the application of pressure to the valve 335. For example, the desired height within the reservoir 228 may be set between marks or other indicia provided on the wall 336.

In the depicted aspirating apparatus 201 as shown in FIG. 3, a manifold 338 may comprise a base 339 that is adapted to couple to the main supply line 225. The base 339 of the manifold 338 may include the striction 227 formed therein. Reservoir 228 may be formed by cooperation of the base 339 and an adjoining portion 340, which may include the wall 336 of translucent or transparent material. The sensor 230 may be coupled to the gas-containing portion 332 of the reservoir 228 and may measure changes in pressure therein. The valve 335 adapted to apply gas pressure to the reservoir 228 may be mounted to the adjoining portion 340.

Figure 4:
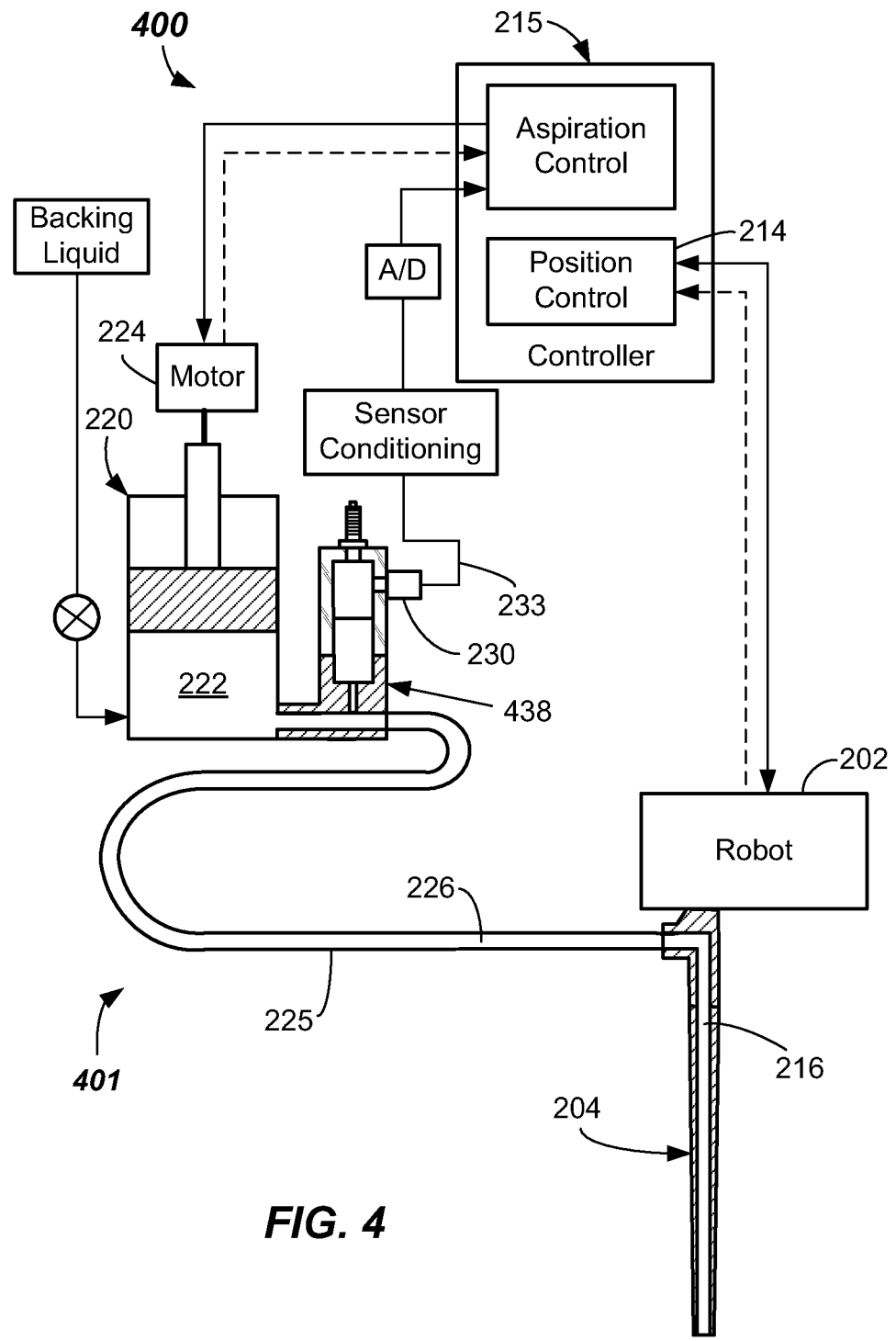
FIG. 4 illustrates a schematic diagram of an alternative aspirating system including an aspirating apparatus according to embodiments.
Figure 5:
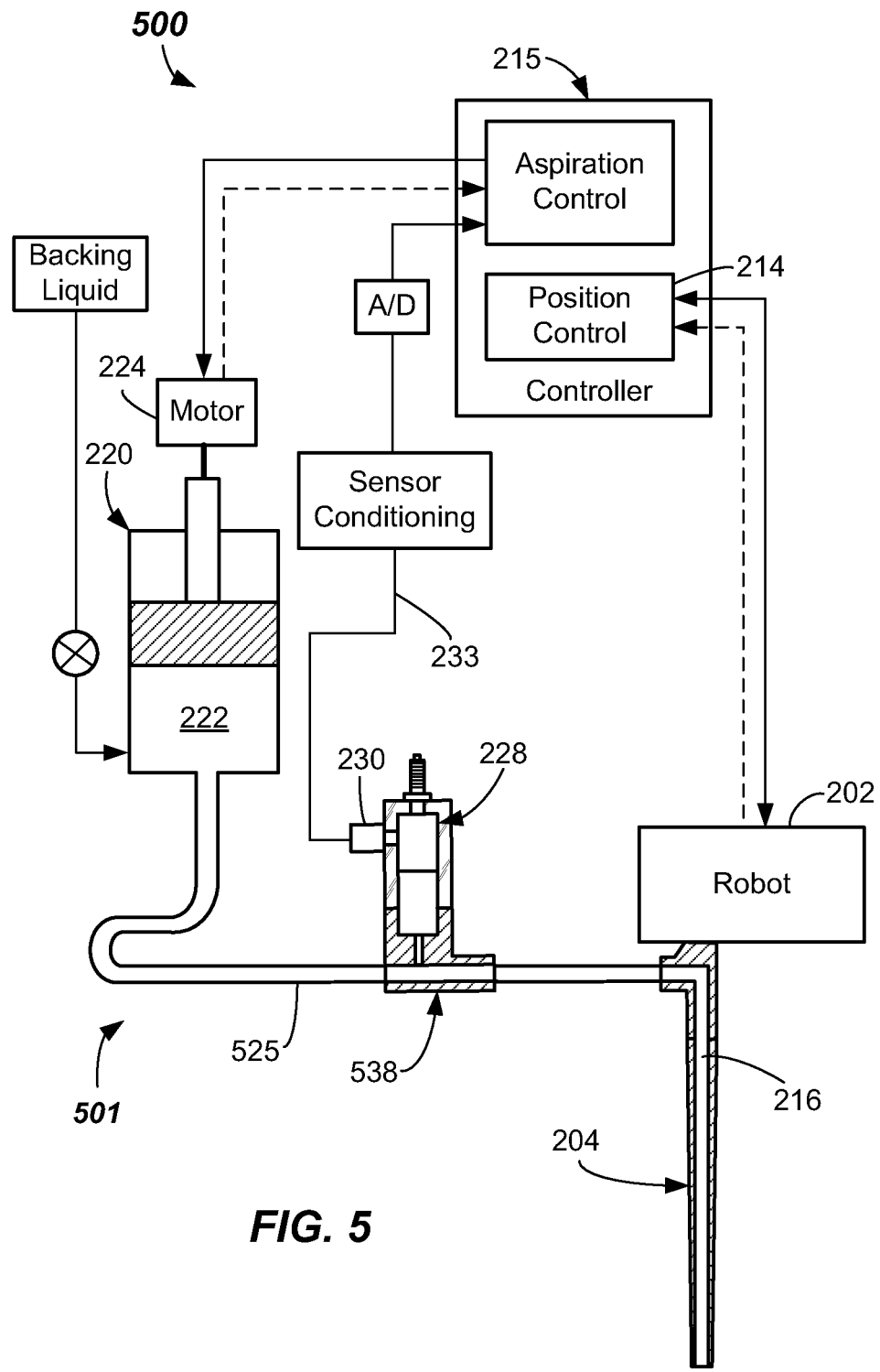
FIG. 5 illustrates a schematic diagram of another alternative aspirating system including an aspirating apparatus according to embodiments.

In the depicted embodiment of the aspiration system 200 of FIGS. 2 and 3, the manifold 338 may be positioned directly adjacent to, or integrated into, the probe 204, as shown. However, the manifold 438 may be positioned directly adjacent to the pump 220 and the pumping chamber 222 in an alternative embodiment of the aspiration system 400 including the aspiration apparatus 401, as shown in FIG. 4. Otherwise, the aspiration apparatus 401 is as previously described. Further, in another alternative embodiment, the manifold 538 may be positioned directly in the main supply line 525 between the probe 204 and the pump 220, as shown in FIG. 5.

In accordance with one or more embodiments, the aspiration control may also be used to verify the effectiveness of the liquid aspiration at low volumes (e.g., less than 25 µL). For example, the aspiration control may determine the presence of air in the interior 216 of the probe 204 at low volumes (e.g., less than 25 µL). In another example, the aspiration control may determine the presence of a clog or other obstruction in the probe 204 at low volumes (e.g., less than 25 µL). In another aspect, an extent of the aspiration shortage (% shortage), if any, may be estimated, as will be apparent from the following.

Referring again to FIGS. 2 and 3, in more detail, the aspiration pressure in the reservoir 228 may be measured by a sensor 230. The sensor 230 is operational and adapted to provide a raw pressure signal in line 233, which may be conventionally filtered and conditioned by sensor conditioning. Sensor conditioning may include a suitable amplifier and a suitable anti-aliasing filter. The anti-aliasing filter may have a cutoff frequency of about 190 Hz or more, for example.

In operation, during aspiration, the robot 202 may position the probe 204 above the container (e.g., 107 or 108) and descend the probe 204. The descent into the container (e.g., 107 or 108) is produced by the robot 202 under the control of the position control 214 until the probe 204 reaches a desired depth therein. Now the aspirator apparatus 201 may be operated via a signal from the aspiration control 217 to draw off a predefined volume of the liquid (e.g., reagent liquid 107R or biological liquid 108S) into the interior 216 of the probe 204. In accordance with a low-volume aspiration embodiment, the aspirated volume is less than about 25 µL, but aspirations larger than about 25 µL could also be performed. As the pump 220 is operated, the level of liquid (e.g., reagent liquid 107R or biological liquid 108S) in the container (e.g., 107 or 108) is attempted to be drawn down (aspirated). When it is determined that a desired volume of liquid (e.g., reagent liquid 107R or biological liquid 108S) has been received within the probe 204, as measured by aspiration control, the pump 220 may be stopped such that no further aspiration of the liquid (e.g., reagent liquid 107R or biological liquid 108S) occurs. This may be determined by a suitable feedback sensor (not shown) on the motor 224 providing feedback on the position of the pump 220 or counting steps of the motor 224 when the motor 224 is a stepper motor, for example. Other suitable position feedback may be provided.

During the aspiration process, a representative raw aspiration pressure may be measured (e.g., the measured aspiration pressure) via the sensor 230 coupled to the reservoir 228. This raw measured pressure in line 233 may be conditioned by sensor conditioning to provide a conditioned measured pressure signal to the aspiration control. Each embodiment may include conversion by an A/D filter. The sampling rate may be at any suitable rate such as 1000 samples per second. The sampling may be continuous for the entire aspiration cycle, or over any representative portion of the aspiration cycle.

Because the raw pressure measurement is devoid of disturbance frequencies by virtue of the decoupling provided by the striction 227, it is now possible using embodiments of the invention to accurately determine the aspiration quality at such low volumes of a liquid. In order to verify the effectiveness (e.g., quality) of the aspiration, the conditioned pressure signal is measured and compared at an evaluation point. At the desired evaluation point, the conditioned pressure signal is compared to a pre-established pressure threshold value. If the conditioned pressure signal is above (has a higher absolute value) the pre-established pressure threshold value, then the aspiration may be deemed to be successful. If the conditioned pressure signal has an absolute value that is below the pre-established pressure threshold value, then the aspiration may be deemed to be unsuccessful or incomplete. This may signify that some air was aspirated (e.g., an air bubble).

Similarly, because the pressure now may be discriminated at such relatively low aspiration volumes, the existence of a clot or other undesirable solid or semisolid material in or on the probe 204 may be determined. Any suitable method known in the art may be used to determine if undesirable material is present using the conditioned pressure signal.

Once it is determined that the aspiration was unsuccessful, remedial measures may include stopping, aspirating from another well in the case of insufficient reagent volume 107R, and/or obtaining additional biological liquid 108S. Optionally, the extent of aspiration shortage may be determined, and if there is an oversupply of the liquid (e.g., liquid reagent), then if the shortage is small enough, then the transfer may be completed. Further, to the extent that a smaller amount of a biological liquid 108S may be aspirated, but where the amount is known, a corresponding smaller amount of reagent liquid 107R may be aspirated for mixing therewith in the reaction vessel 113.

Figure 6:
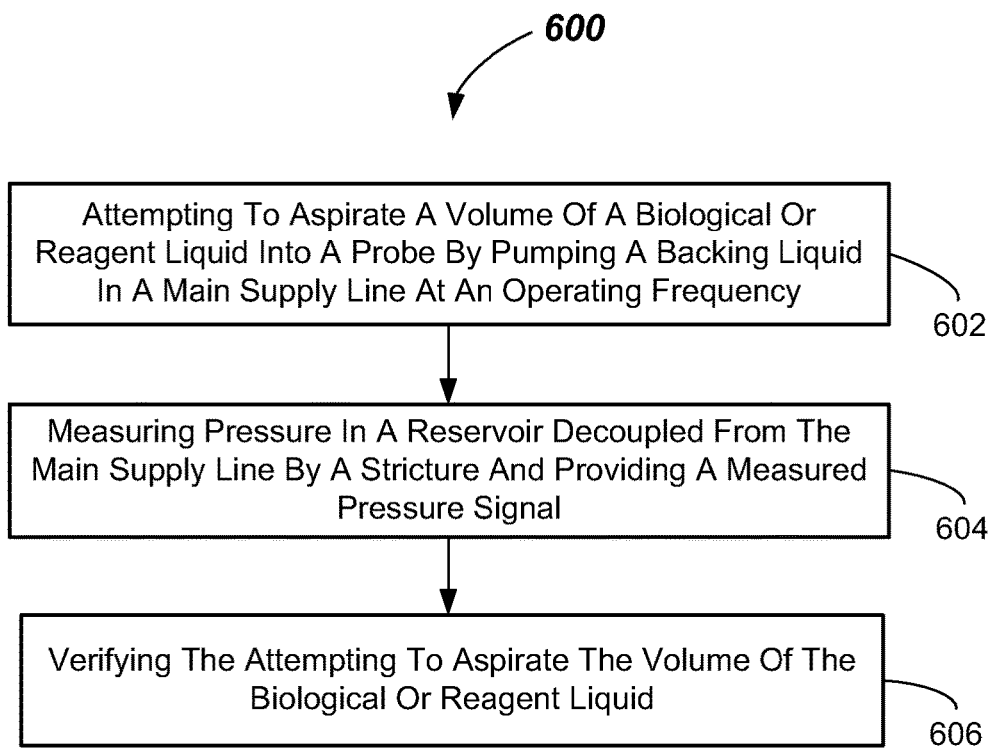
FIG. 6 is a flowchart illustrating methods according to embodiments.

Referring now to FIG. 6, a broad method of aspirating a biological liquid or reagent liquid is illustrated. The method 600 includes, in 602, attempting to aspirate a volume of the biological liquid (e.g., biological liquid 108S) or reagent liquid (e.g., reagent liquid 107R) into a probe (e.g., probe 204) by pumping a backing liquid (e.g., backing liquid 226) in a main supply line (e.g., main supply line 225) at an operating frequency, measuring pressure in a reservoir (e.g., reservoir 228) decoupled from the main supply line by a striction (e.g., striction 227) and providing a measured pressure signal in 604, and verifying the attempting to aspirate the volume of the biological or reagent liquid in 606.

Based upon the measured pressure signal, having relatively low noise, it may be verified if a correct amount of the biological liquid or reagent liquid was actually aspirated in an aspiration cycle (a cycle begins at the start of the aspiration and ends at the end of the aspiration). An estimate of the percent shortage may be provided as well, as explained above. The method 600 is particularly effective when aspirating at relatively-low volumes, such as when the total aspirated volume per aspiration cycle is 25 µL or less.

The quality of the liquid aspiration may be determined by comparing a conditioned pressure signal magnitude to a predetermined pressure signal threshold value at an evaluation point. The comparison of the conditioned pressure signal magnitude to the predetermined pressure signal threshold value may be achieved at a portion of the aspiration cycle where greater than 50% of a total volume to be aspirated in the aspiration cycle should have been aspirated (in a full aspiration), or even where nearly all (greater than 90%) of a total volume to be aspirated in the aspiration cycle should have been aspirated (in a full aspiration). In some embodiments, the predetermined pressure threshold value may be based upon a percentage of an air aspiration baseline.

Having shown the preferred embodiments, those skilled in the art will realize many variations are possible that will still be within the scope of the claimed invention. Therefore, it is the intention to limit the invention only as indicated by the scope of the claims.

What is claimed is:

1. An aspirating apparatus, comprising:
   a pump operable at an operating frequency, the pump optionally including a pumping chamber;
   a probe having a probe interior;
   a main supply line containing a backing liquid coupled to and extending from the pump, the main supply line including the probe interior;
   a striction coupled to the main supply line, or the pump chamber, if present; and
   a reservoir fluidly coupled to the striction, wherein the striction is sized to minimize flow through the striction at one or more disturbance frequencies above the operating frequency.

2. The aspirating apparatus of claim 1, comprising a sensor coupled to the reservoir.

3. The aspirating apparatus of claim 2, wherein the sensor produces a measured sensor signal that is devoid of disturbances produced by flow in the main supply line that are above the operating frequency.

4. The aspirating apparatus of claim 1, wherein the reservoir comprises a liquid-containing portion and a gas-containing portion.

5. The aspirating apparatus of claim 1, wherein the striction is sized to substantially minimize flow of the backing liquid through the striction at greater than about 50 Hz.

6. The aspirating apparatus of claim 1, wherein the reservoir comprises a valve adapted to apply gas pressure to the reservoir.

7. The aspirating apparatus of claim 1, wherein the reservoir includes a wall of a transparent or translucent material.

8. The aspirating apparatus of claim 1, wherein the striction is sized to eliminate flow of the backing liquid through the striction at the one or more disturbance frequencies.

9. The aspirating apparatus of claim 1, wherein the striction has a striction cross-sectional area (As) that is less than a main supply line cross-sectional area (Am) of the main supply line.

10. The aspirating apparatus of claim 1, wherein the reservoir and the striction are included in a manifold.

11. The aspirating apparatus of claim 10, wherein the manifold is positioned directly adjacent to, or integrated into, the probe.

12. The aspirating apparatus of claim 10, wherein the manifold is positioned directly adjacent to the pump.

13. The aspirating apparatus of claim 10, wherein the manifold is positioned directly in the main supply line.

14. The aspirating apparatus of claim 10, wherein the manifold comprises a base including the striction, the reservoir including a translucent or transparent wall, a sensor coupled to the reservoir, and a valve adapted to apply gas pressure to the reservoir.

15. A method of aspirating a biological or reagent liquid, comprising:
    attempting to aspirate a volume of the biological or reagent liquid into a probe by pumping a backing liquid in a main supply line at an operating frequency;
    measuring pressure in a reservoir decoupled from the main supply line by a striction sized to minimize flow of the backing liquid through the striction at one or more disturbance frequencies above the operating frequency, and providing a measured pressure signal; and
    verifying the attempting to aspirate the volume of the biological or reagent liquid.

16. The method of claim 15, comprising sizing the striction to eliminate flow of the backing liquid through the striction at one or more disturbance frequencies.

17. The method of claim 15, comprising applying gas pressure to the reservoir.

18. The method of claim 15, comprising coupling a sensor to the reservoir to provide the measured pressure signal.

19. The method of claim 15, wherein the measuring pressure in the reservoir comprises directly measuring pressure of a gas contained in the reservoir.

20. An aspiration system, comprising:
- a probe having a probe interior adapted to aspirate a biological liquid or reagent liquid;
- a pump having a pumping chamber operable at an operating frequency;
- a robot coupled to and adapted to move the probe;
- a main supply line containing a backing liquid coupled to the pumping chamber, the main supply line including the probe interior;
- a striction coupled to the pumping chamber or main supply line; and
- a reservoir fluidly coupled to the striction, wherein the striction is sized to decouple the reservoir and minimize flow of backing liquid at one or more disturbance frequencies above the operating frequency.

* * * * *